US006096302A

United States Patent [19]
Kandel et al.

[11] Patent Number: 6,096,302
[45] Date of Patent: Aug. 1, 2000

[54] ASSAY FOR THE MEASUREMENT OF NEURONAL DEGRADATION AND USES THEREOF

[75] Inventors: Eric R. Kandel, Riverdale; Mary E. Bach, Bronx, both of N.Y.; Min Zhuo, St. Louis, Mo.

[73] Assignee: The Trustees of Columbia University in the City of New York, New York, N.Y.

[21] Appl. No.: 08/725,876

[22] Filed: Oct. 4, 1996

Related U.S. Application Data

[60] Provisional application No. 60/004,887, Oct. 6, 1995.
[51] Int. Cl.$^7$ ............................. G01N 33/567; C12N 5/06
[52] U.S. Cl. ......................... 424/93.1; 435/325; 435/1.1; 435/1.2; 435/4; 436/503
[58] Field of Search ..................................... 128/630, 731; 435/1.1, 1.2, 3, 4, 325; 424/93.1; 436/503

[56] References Cited

U.S. PATENT DOCUMENTS 5,059,612 10/1991 Imanishi et al. .
5,362,915 11/1994 Maschler et al. .

FOREIGN PATENT DOCUMENTS

WO9115451 10/1991 WIPO .

OTHER PUBLICATIONS

Jarooqui et al., *J. Neurosci. Res.*, vol. 38, pp. 6–11, 1994.
Huang et al., *PNAS*, vol. 92, pp. 2446–2450, Mar., 1995.
Huang et al., *Cell*, vol. 79, pp. 69–79, Oct. 7, 1994.
Nguyen et al., *Science*, vol. 265, pp. 1104–1107, Aug. 1994.
Frey et al., *Science*, vol. 260, pp. 1661–1664, 1993.
Wagner et al., *Pharmacol., Biochem., Beh.*, vol. 45, pp. 455–464, 1993.
Deupree et al., *Brain Res.*, vol. 554, pp. 1–9, 1991.
Silva et al, *Science*, vol. 257, pp. 201–206, 1992.
Silva et al., *Science*, vol. 257, pp. 206–211, 1992.
Barnes, C. A. *Trends Neurosci.* 17, 13–18 (1994)(Exhibit 5).
Bliss, T. V. P. & Collingridge, G. L. *Nature* 361, 31–39 (1993)(Exhibit 6).
Castrén, Eero, *NeuroReport* 4(7), 895–898 (1993)(Exhibit 7).
Davies, A. M. *Nature* 368, 193–194 (1994)(Exhibit 8).
Dechant, G., Rodriguez–Tébar, A. & Barde, Y.–A. *Prog. Neurobiol.* 42, 347–352 (1994) (Exhibit 9).
Dudek, S. M. & Bear, M. F. *Proc. Natl. Acad. Sci. USA* 89, 4363–4367 (1992)(Exhibit 10).
Fischer, W., Sirevaag, A., Wiegand, S. J., Lindsay, R. M. & Bjorklund, A. *Proc. Natl. Acad. Sci. USA* 91, 8607–8611 (1994)(Exhibit 11).
Frey, U., Huang, Y.–Y. & Kandel, E. R. *Science* 260, 1661–1664 (1993)(Exhibit 12).
Harrison, C.M. and B.E. Alger. *Brain Research* 602, 175–179 (1993)(Exhibit 13).
Huang, Y.–Y. & Kandel, E. R. *Learning & Memory* 1, 74–82 (1994)(Exhibit 14).
Klann, Eric et al. *Proc. Natl. Acad. Sci. USA* 90, 8337–8341 (1993)(Exhibit 15).
Klann, Eric et al. *The Journal of Biological Chemistry* 266(36), 24253–24256 (1991)(Exhibit 16).
Klein, R. *FASEB J.* 8, 738–7440 (1994)(Exhibit 17).
Larson, John et al., *Brain Research* 368, 347–350 (1986)(Exhibit 18).
Nguyen, P.V., Abel, T. & Kandel, E.R. *Science* 265,1104–1107 (1994)(Exhibit 19).
O'Dell, T.J. & Kandel, E.R. *Learning & Memory* 1, 129–139 (1994)(Exhibit 20).
Randt, Clark T. et al. *Pharmacology, Biochemistry & Behavior* 17, 677–680 (1982)(Exhibit 21).
Weishaar, Ronald E. *Journal of Medicinal Chemistry* 28(5), 537–545 (1985)(Exhbit 22).
Xie, Zheng and Bhagavatula R. Sastry. *Brain Research* 604, 173–179 (1993)(Exhibit 23).
Zafra, Francisco et al. *Proc. Natl. Acad. Sci. USA* 88(22), 10037–10041 (1991)(Exhibit 24).

*Primary Examiner*—Gary L. Kunz
*Assistant Examiner*—Stephen Gucker
*Attorney, Agent, or Firm*—John P. White; Cooper & Dunham LLP

[57] ABSTRACT

The present invention provides a method to determine the extent of neuronal degradation due to aging, a learning disability, or a neurological disorder, which includes: (a) stimulating a neuronal cell population under suitable conditions so as to induce a late-phase long term potentiation; (b) stimulating a normal neuronal cell population under suitable conditions so as to induce a late-phase long term potentiation; and (c) comparing the duration of the late-phase long term potentiation of the neuronal cell population in step (a) with that of the normal neuronal cell population of step (b) so as to determine the extent of neuronal degradation due to aging, the learning disability or the neurological disorder. The learning disability or neurological disorder may be Alzheimer's Disease, a degenerative disorder associated with learning, memory or cognitive dysfunction, cerebral senility, multi-infarct dementia and senile dementia, electric shock induced amnesia or amnesia.

11 Claims, 16 Drawing Sheets

Young (3 weeks)

Aged (18-30 mos)

1mv

10ms

NGF TREATMENT

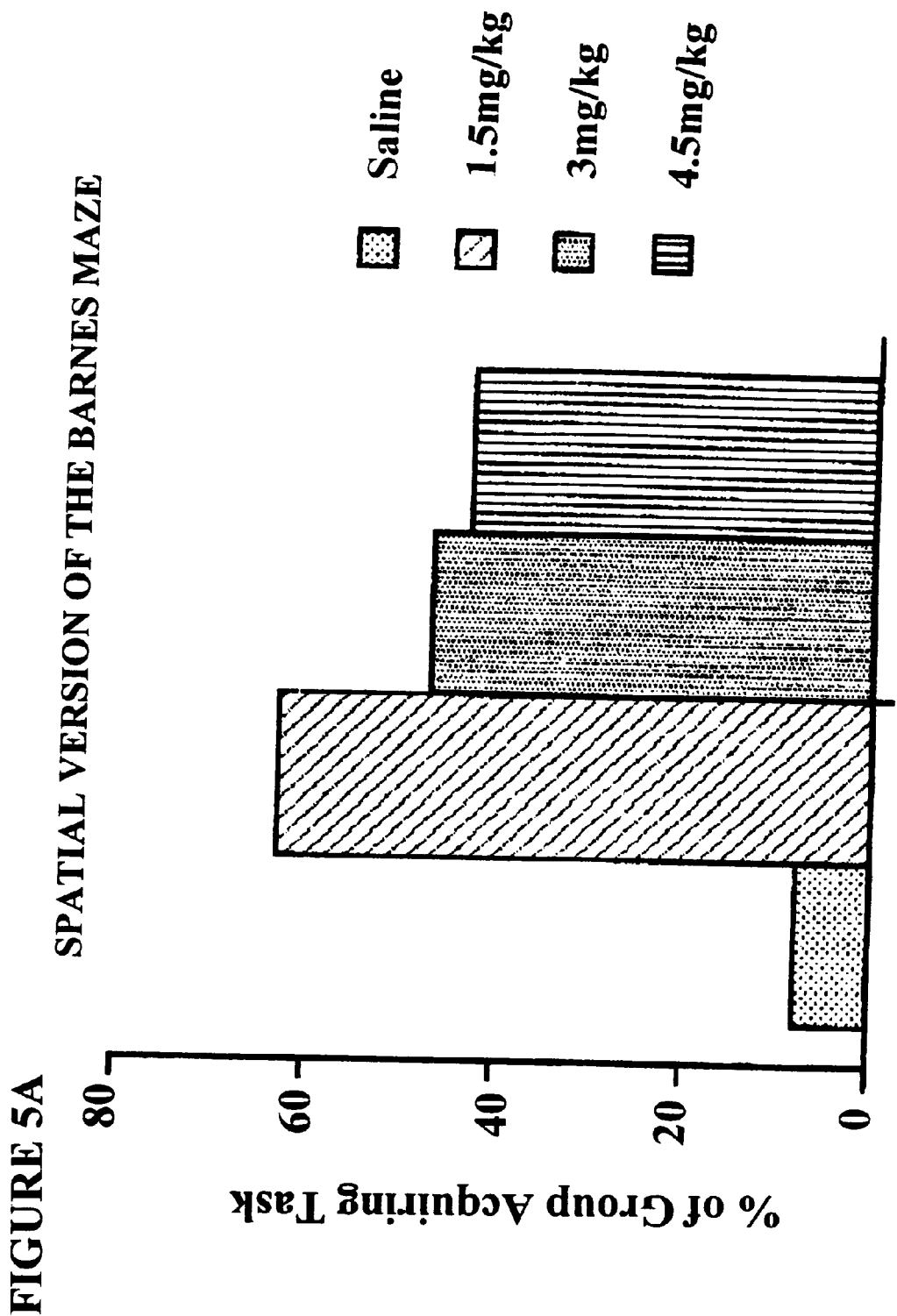

ASSAY FOR THE MEASUREMENT OF NEURONAL DEGRADATION AND USES THEREOF

This application claims the benefit of U.S. Provisional Application No.60/004,887, filed Oct. 6, 1995, the contents of which are hereby incorporated by reference into the present application.

BACKGROUND OF THE INVENTION

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

An age related decline in explicit forms of memory has been consistently observed in various species including human, non-human primates and rodents (Gage et al., 1989; Barnes, 1994). In experimental animals, including monkeys, rats, and mice, age is also accompanied by a loss of explicit forms of learning and memory evident in spatial tasks (deToledo-Morell et al., 1988; Aggleton et al., 1989; Fischer et al., 1989). The search for central loci in the brain responsible for these changes in explicit memory and. defining the cellular and molecular mechanisms that lead to such changes is the focus of many researchers. Among the many model systems used to study this phenomena, the hippocampus and its related structures have been the most intensively studied in aging (Landfield, 1988; Barnes, 1994). The hippocampus and its related temporal lobe structures are important for explicit forms of memory (Squire & Zola-Moran, 1991; Squire, 1992). Interestingly, severe cases of explicit memory impairment and loss are seen in patients with amnesia or Alzheimer's disease which are known to have hippocampal disruptions. Hippocampal long-term potentiation (LTP) is a well established cellular model for memory storage (Bliss & Collingridge, 1993).

SUMMARY OF THE INVENTION

The present invention provides a method to determine the extent of neuronal degradation due to aging, a learning disability, or a neurological disorder, which includes: (a) stimulating a neuronal cell population under suitable conditions so as to induce a late-phase long term potentiation (L-LTP); (b) stimulating a normal neuronal cell population under suitable conditions so as to induce a late-phase long term potentiation; and (c) comparing the duration of the late-phase long term potentiation of the neuronal cell population in step (a) with that of the normal neuronal cell population of step (b) so as to determine the extent of neuronal degradation due to aging, the learning disability or the neurological disorder. The learning disability or neurological disorder may be Alzheimer's Disease, a degenerative disorder associated with learning, memory or cognitive dysfunction, cerebral senility, multi-infarct dementia and senile dementia, electric shock induced amnesia or amnesia.

BRIEF DESCRIPTION OF THE FIGURES

(FIG. 1A) Distribution of maximal amplitudes of field excitatory postsynaptic potentials (EPSPs) for four age groups. (FIG. 1B) Average maximal amplitude of EPSPs shown in (FIG. 1A). The EPSPs are significantly smaller in adult and aged mice than in young or young adult mice. (FIG. 1C) Representative records of the EPSP by paired-pulse stimulation at 50 milliseconds (msec) interpulse intervals. (FIG. 1D) Average paired-pulse facilitation tested at different interpulse intervals (25, 50, 100, 150, 200, 300 and 400 msec) in mice of four different ages. Paired-pulse facilitation was significantly attenuated in adult and aged mice. Data are presented as mean±SEM.

(FIG. 2A) The early phase of LTP (E-LTP) induced by one train of tetanus stimulation (100 Hz, 1 sec) was not affected by aging. The average prevalues were 0.48 mV/msec (aged) and 0.49 mV/msec (young). (FIG. 2B) Summary of the average E-LTP of the four different age groups. (FIG. 2C) Four-train stimulation (four at 100 Hz, 1-sec trains at 5-min intervals) produced long-lasting potentiation of synaptic transmission. The average EPSP was significantly enhanced in young (3 months) mice 1, 2 and 3 hours after stimulation. By contrast, in middle-aged and aged mice, the late phase potentiation was diminished.

(FIG. 3A) In young mice nerve growth factor (NGF) (1 ng/ml) alone or paired with weak stimulation (25 Hz, 1 sec) did not produce significant potentiation. NGF (1 ng/ml) reversed the loss of L-LTP in aged mice. (FIG. 3B) In young mice NT-4/5 (1 ng/ml) produced long-lasting enhancement of synaptic response when paired with weak stimulation (25 Hz, 1 sec). NT-4/5, a neurotrophic factor, alone did not produce significant enhancement. (Inset) Representative records of the EPSP before and after NT-4/5 paired training. NT-4/5, reversed the loss of L-LTP in aged mice (1 ng/ml, mean 229.9±30.8%, n=6; closed squares). In two experiments, a second pathway was also recorded and NT-4/5 did not significantly affect the EPSP over the period of recording (data not shown). NT-4/5 treatment did not significantly affect post-tetanic potentiation. The average prevalues were 0.56 mV/msec (control) and 0.38 mV/msec (NT-4/5 treated). (Inset) Representative records of the EPSP before and 3 hr after strong tetanic stimulation. (FIG. 3C) Summary data of the effects of different neurotrophic factors on L-LTP. (FIG. 3D) The D1/D5 agonist, 8-Br-ApB (5 $\mu$M) induced long-lasting enhancement of synaptic responses in both young and aged mice.

(FIG. 4A) Percentage of young adult, adult, middle-aged and aged male C57 mice that acquired the spatial version of the barnes circular maze. (FIG. 4B) Mean number of errors made by the four different age groups across session blocks comparised of 5 sessions. (FIG. 4C) Comparison of L-LTP in mice is classified based on impaired or unimpaired hippocampal dependent learning and memory performance on the Barnes maze. The data was collapsed across age groups based on spatial memory performance.

FIGS. 5A–5B: Attenuation of spatial memory impairment by D1/D5 agonist SKF 38393 in aged (18 months) C57 mice. (FIG. 5A) Percentage of the four different dose groups (0.0, 1.5, 3 or 4.5 mg/kg SKF 38393) of aged male C57 mice that acquired the spatial version of the Barnes circular maze. Significantly more of the aged mice that received SKF 38393 (i.p. 40 min prior to testing) acquired the Barnes maze comared to aged mice that received saline. (FIG. 5B) Mean number of errors made by the four different dose groups across session blocks comprised of 5 sessions. Prior to drug adminsitration (Sessions 1–14) there was no differene in amount of errors made between the aged mice dose groups. During the last 5 sessions, the group that received 1/5 mg/kg of SKF 38393 was found to make significantly fewer errors than the aged group that received saline.

DETAILED DESCRIPTION OF THE INVENTION

Figure 1A:
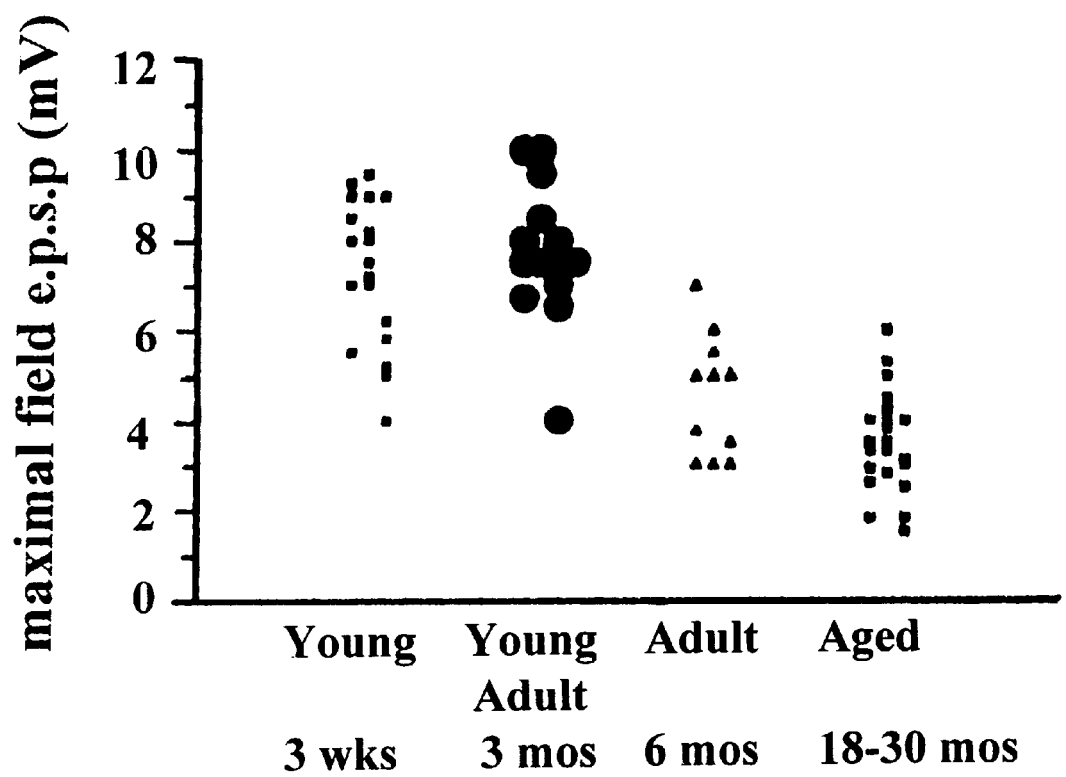
FIG. 1A–1D: Age-dependent decreases of synaptic transmission and paired-pulse facilitation in the CA1 region of hippocampus.
Figure 1B:
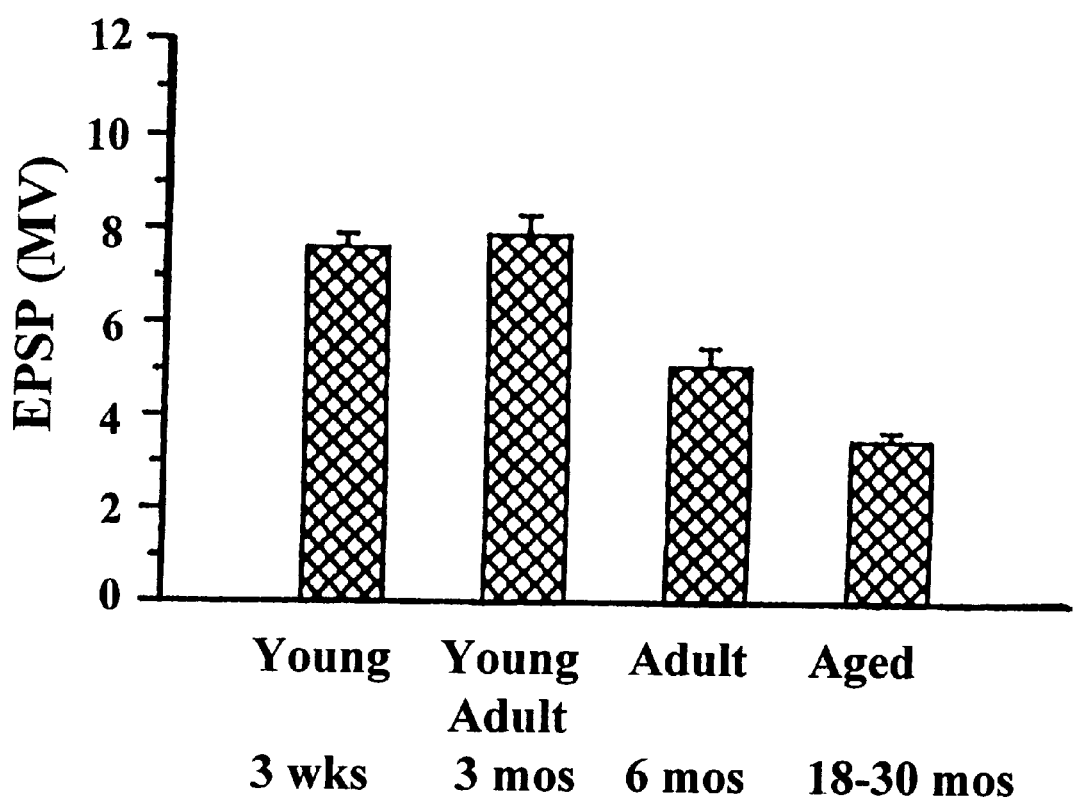
Figure 1C:
Figure 1C:

The present invention provides an improved method to determine the extent of neuronal degradation due to aging, a learning disability, or a neurological disorder, which includes: (a) stimulating a neuronal cell population under suitable conditions so as to induce detectable late-phase long term potentiation; (b) stimulating a normal neuronal cell population under suitable conditions so as to induce a late-phase long term potentiation; and (c) comparing the duration of the late-phase long term potentiation of the neuronal cell population in step (a) with that of the normal neuronal cell population of step (b) so as to determine the extent of neuronal degradation due to aging, the learning disability or the neurological disorder.

The neuronal cell population may be an aged neuronal cell population, an electrically stimulated neuronal cell population, or a cell population associated with a learning disability or a neurological disorder. The neuronal cell population may be from the CA1 or CA3 region of the hippocampus.

As used herein, the term "neuronal degradation" includes morphological and functional deterioration of neuronal cells characteristic of degeneration associated with age or characteristic of an association with a neurological disorder. "Neuronal degradation" also includes cognitive impairments which may be associated with aging, Alzheimer's disease, amyotrophic lateral sclerosis, chronic peripheral neuropathy, drug or alcohol use, electroshock treatment or trauma, Guillain-Barre syndrome, Huntington's disease, a learning disability, a memory deficiency, a mental illness, myasthenia gravis, Parkinson's disease and reduction in spatial memory retention.

As used herein, the term "learning disability" includes a hippocampal learning or memory deficit concurrent with an electrophysiological deficit. This term applies to young adult subjects (for example, mice 12 weeks old) and adult subjects (for example, mice 6 months old) that show behavioral impairments and have a corresponding electrophysiological deficit.

As used herein, the term "stimulating a neuronal cell population" includes electrical stimulation to an evoke electrophysiological response from the neuronal cell population, treating the neuronal cell population with a compound or a drug to elicit a response, applying tetani to the neuronal cell population to elicit a electrophysiological response, treating a subject with a compound which compound is capable of stimulating the neuronal cell population of the subject or perfusing a solution containing a composition or compound over the neuronal cell population. The response may be late phase long term potentiation, early phase long term potentiation. The neuronal cell population may be in a hippocampal slice in vitro, in a subject in vivo, or in other neuronal tissue.

As used herein, the term "suitable conditions" includes electrophysiological stimulation conditions which are capable of producing a late-phase long term potentiation. The suitable conditions include stimulating hippocampal slices from aged mammals under physiological conditions with at least one (1) train of about 100 Hertz tetanus for about 1 second to evoke an early-phase LTP (E-LTP) response or about four (4) trains of 100 Hertz tetanus for about 1 second at about 5 minute intervals to evoke a late phase long term potentiation (L-LTP) response. The suitable conditions may also include a stimulation of about four trains, performed at about 5 minute intervals, wherein each train is about 100 Hertz stimulation for about 0.2 millisecond intervals performed over a duration of about 1 second. The late-phase long term potentiation may be sustained longer than about 3 hours following the stimulus. The suitable conditions may include a stimulation of about four trains, performed at about 5 minute intervals, wherein each train is about 100 Hertz stimulation for about 0.2 millisecond intervals performed over a duration of about 1 second.

As used herein, the term "normal neuronal cell population" includes a neuronal cell population derived from a subject which does not appear to have neuronal degradation due to aging, a neurological disorder, a learning disability, exposure to trauma or electric shock.

As used herein, the term "cognitive disorder" includes a learning disability or a neurological disorder which may be Alzheimer's Disease, a degenerative disorder associated with learning, a learning disability, memory or cognitive dysfunction, cerebral senility, multi-infarct dementia and senile dementia, electric shock induced amnesia or amnesia.

The present invention also provides for a method for determining if a compound is capable of alleviating symptoms of a cognitive disorder of memory or a learning disability, which includes: (a) contacting a neuronal cell population associated with the cognitive disorder with the compound under suitable conditions; (b) stimulating the neuronal cell population of step (a) under suitable conditions so as to induce a late-phase long term potentiation; and(c) comparing the duration of the latephase long term potentiation of the neuronal cell population of step (b) with that of the duration in the absence of compound so as to determine if the compound is capable of alleviating the symptoms of the cognitive disorder of memory or a learning disability. The cognitive disorder may be Alzheimer's disease, a learning disability, electric shock induced amnesia or amnesia.

Another embodiment of the subject invention is a method for treating a subject with a cognitive disorder of memory or a learning disability which comprises administering to the subject a therapeutically effective amount of a compound discovered by the methods above to be capable of alleviating the symptoms of the cognitive disorder of memory or the learning disability in the subject thereby treating the cognitive disorder of memory or the learning disability in the subject.

The compound may be capable of increasing the duration of the late-phase long term potentiation of the neuronal cells of the subject. The compound may be associated with a suitable pharmaceutically acceptable carrier.

The subject may be a mammal or a human subject. The administration may be intralesional, intraperitoneal, intramuscular or intravenous injection; infusion; liposome-mediated delivery; gene bombardment; topical, nasal, oral, anal, ocular or otic delivery.

In the practice of any of the methods of the invention or preparation of any of the pharmaceutical compositions an "therapeutically effective amount" is an amount which is capable of alleviating the symptoms of the cognitive disorder of memory or learning in the subject. Accordingly, the effective amount will vary with the subject being treated, as well as the condition to be treated. For the purposes of this invention, the methods of administration are to include, but are not limited to, administration cutaneously, subcutaneously, intravenously, parenterally, orally, topically, or by aerosol.

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions including therapeutically effective amounts of protein compositions and compounds capable of alleviating the symptoms of the cognitive disorder of memory or learning in the subject of the invention together with suitable diluents, preservatives, solubilizers, emulsifiers, adjuvants and/or carriers useful in treatment of neuronal degradation due to aging, a learning disability, or a neurological disorder. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the compound or composition. The choice of compositions will depend on the physical and chemical properties of the compound capable of alleviating the symptoms of the cognitive disorder of memory or the learning disability in the subject.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

Portions of the compound of the invention may be "labeled" by association with a detectable marker substance (e.g., radiolabeled with $^{125}I$ or biotinylated) to provide reagents useful in detection and quantification of compound or its receptor bearing cells or its derivatives in solid tissue and fluid samples such as blood, cerebral spinal fluid or urine.

When administered, compounds are often cleared rapidly from the circulation and may therefore elicit relatively shortlived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The compound of the present invention capable of alleviating symptoms of a cognitive disorder of memory or learning may be delivered in a microencapsulation device so as to reduce or prevent an host immune response against the compound or against cells which may produce the compound. The compound of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

Another embodiment of the present invention is a method for diagnosing a cognitive disorder of learning or memory in a subject which includes: (a) stimulating a neuronal cell population of the subject and a normal control neuronal cell population under suitable conditions so as to induce latephase long term potentiation, (b) measuring the duration of the late-phase long term potentiations of step (b) and thus diagnosing a cognitive disorder of learning or memory in the subject. The cognitive disorder may be Alzheimer's disease, a learning disability, electric shock induced amnesia or amnesia.

This invention is illustrated in the Experimental Detail section which follows. These sections are set forth to aid in an understanding of the invention but are not intended to, and should not be construed to, limit in any way the invention as set forth in the claims which follow thereafter.

Experimental Details

Age-related changes of long-term potentiation in the hippocampus and behavioral spatial memory.

LTP has been systematically examined in the CA1 region of the hippocampus of mice of different ages. These in vitro electrophysiological measures were correlated with performance on an explicit memory task in the same mice. LTP is affected by the aging process. Although the early-phase LTP induced by a single train tetanus was not found to be affected in old mice, the late-phase LTP induced by a multiple train tetanus was significantly decreased in aged and middle-aged mice as compared with young or young adult mice.

Introduction

Mice live slightly over two years and begin to show significant signs of aging at about 18 months. To study possible age-related effects of synaptic transmission and plasticity in the CA1 region of hippocampus, mice were divided into five different age groups: (1) young, 3–7 weeks of age, (2) young adult, 3 months, (3) adult, 6 months, (4) middle-aged, 12 months and (5) aged, 18–30 months. Basal synaptic transmission was first tested in response to electrical stimulation of the Schaffer/commissural collateral pathway and found that synaptic transmission was attenuated in aged mice. In young mice the mean maximal field excitatory postsynaptic potential (EPSP) was 7.6±0.3 mV (n=17), whereas the maximal EPSP in young adult mice was 7.9±0.4 mv (n=14). However, the maximal field EPSP was smaller both in adult (5.1±0.4 mV; n=18) and in aged mice (3.5±0.2 mV; n=25) (FIG. 1).

Figure 1D:
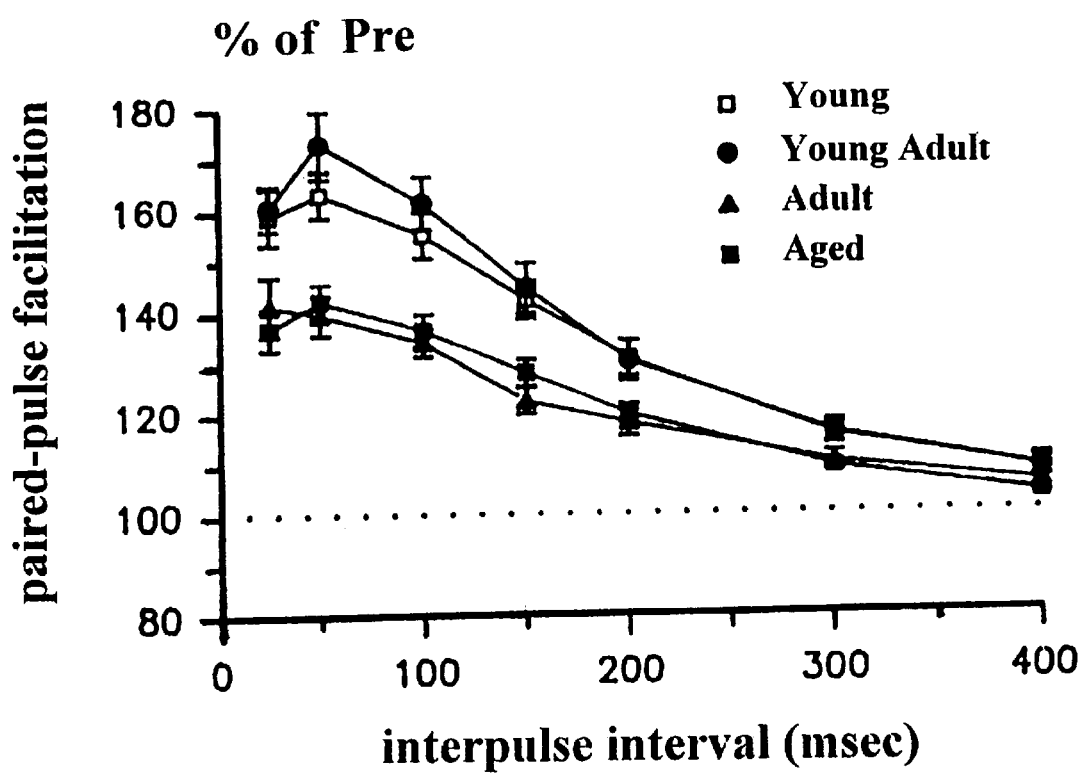

Next paired-pulse facilitation was tested with different interpulse intervals (25–400 msec) in four different groups. In young mice, paired-pulse facilitation was observed between 25 msec and 300 msec, and maximal paired-pulse facilitation was 163.0±4.6% (n=23) at 50 msec interpulse intervals. Similar magnitude of paired-pulse facilitation was observed in young adult mice (FIG. 1D). By contrast, in both adult and old mice, paired-pulse facilitation was significantly decreased between 25 msec and 200 msec interpulse intervals as compared with that in young or adult mice (FIG. 1D). At 50 msec interpulse interval, when paired-pulse facilitation is at its maximum, it was 139.6±3.6% (n=28) in old mice and 144.8±3.5% (n=14) in middle-aged mice.

Figure 2A:
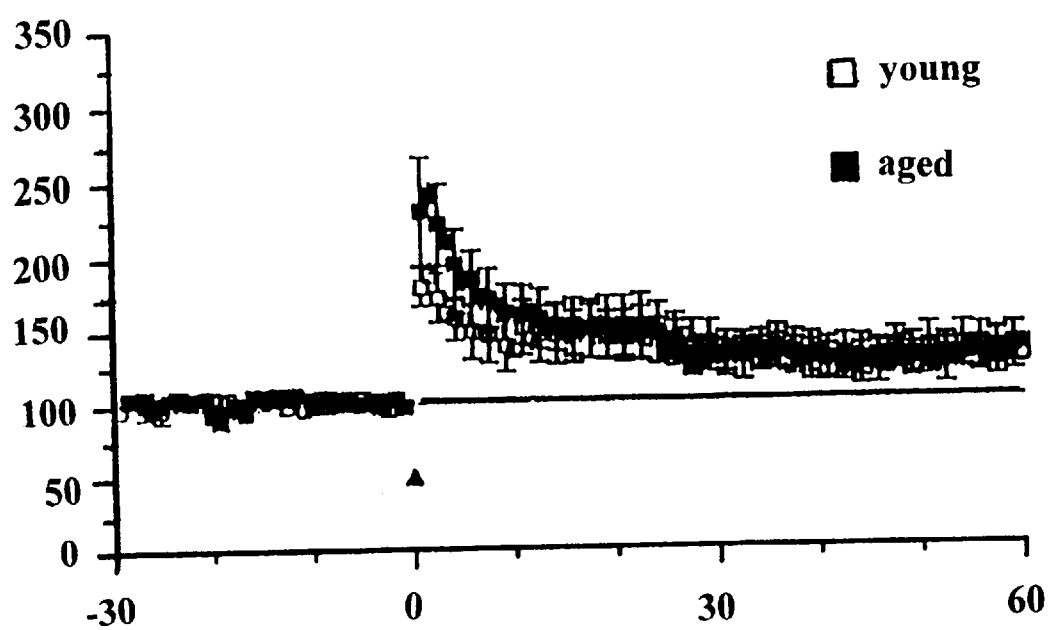
FIGS. 2A–C: Loss of the late phase but not the early phase of LTP in aged mice.
Figure 2B:
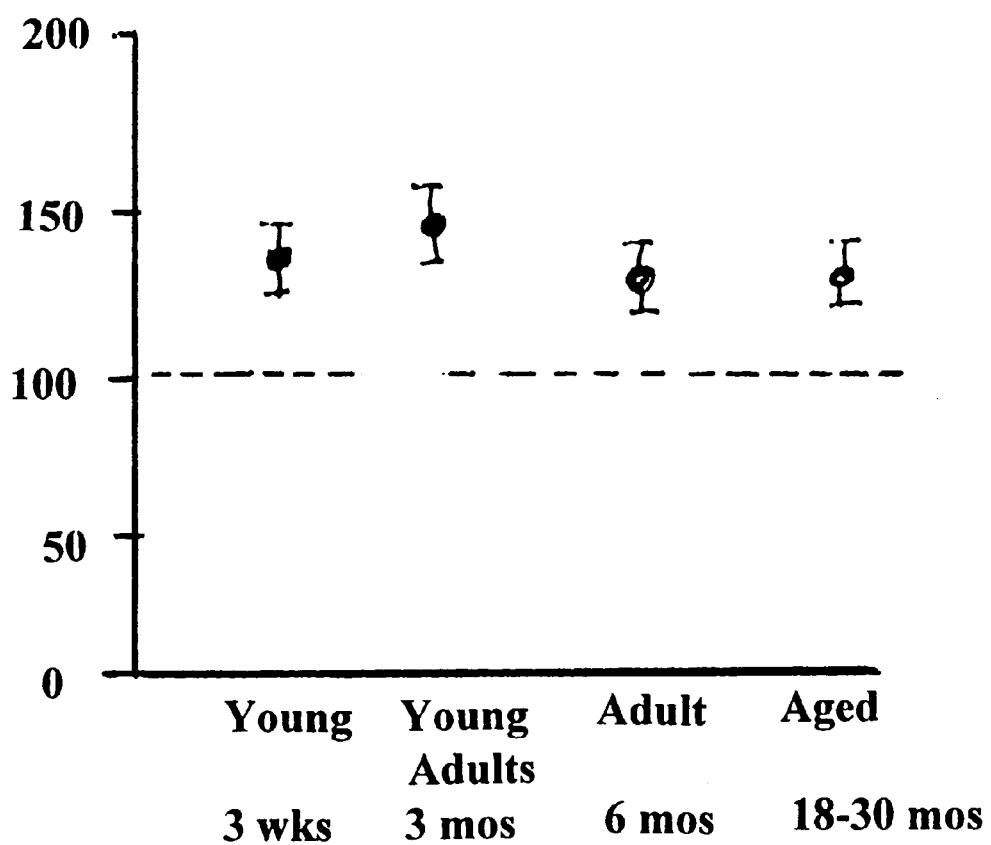
Figure 2C:
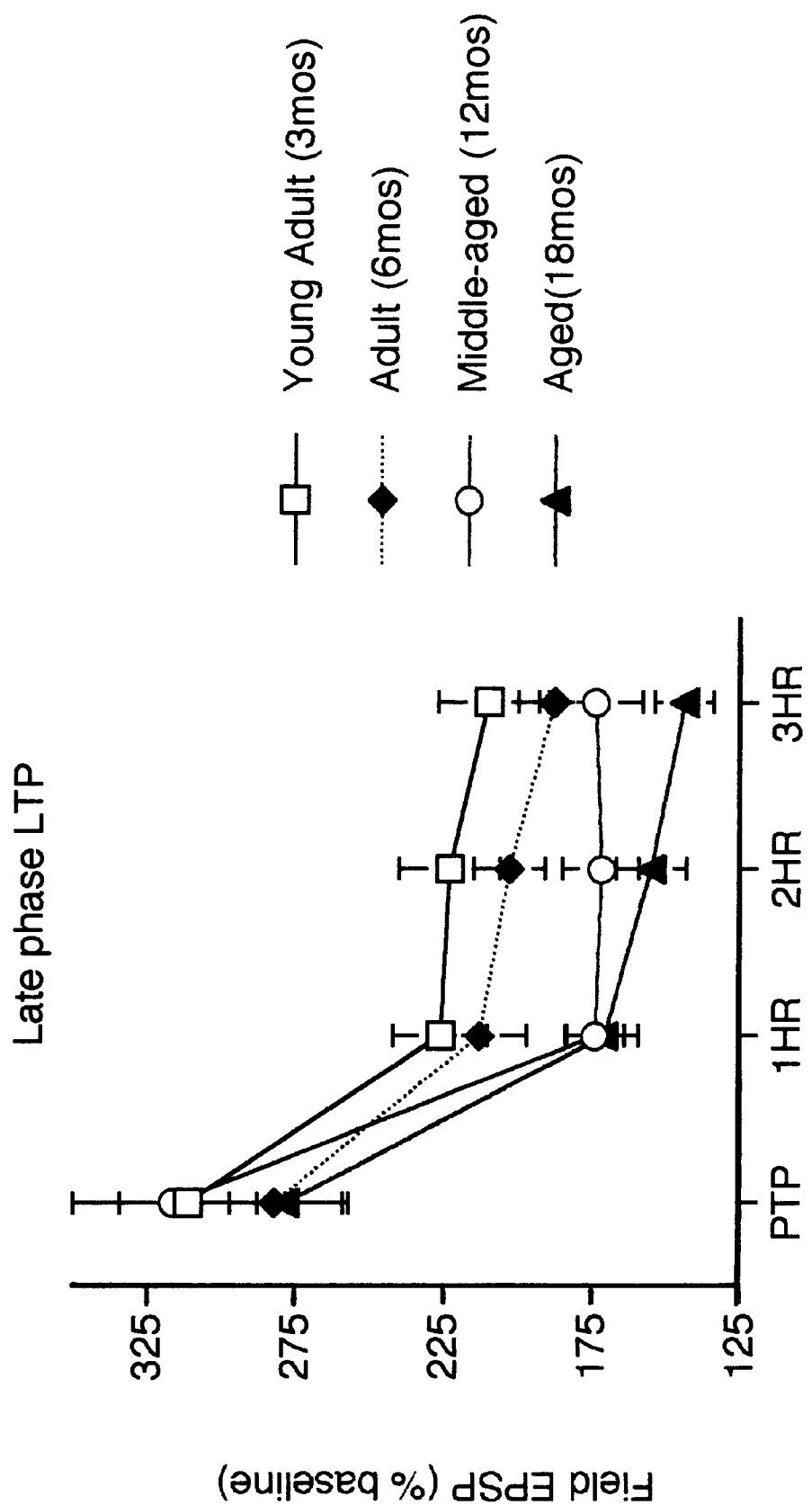
Figure 3A:
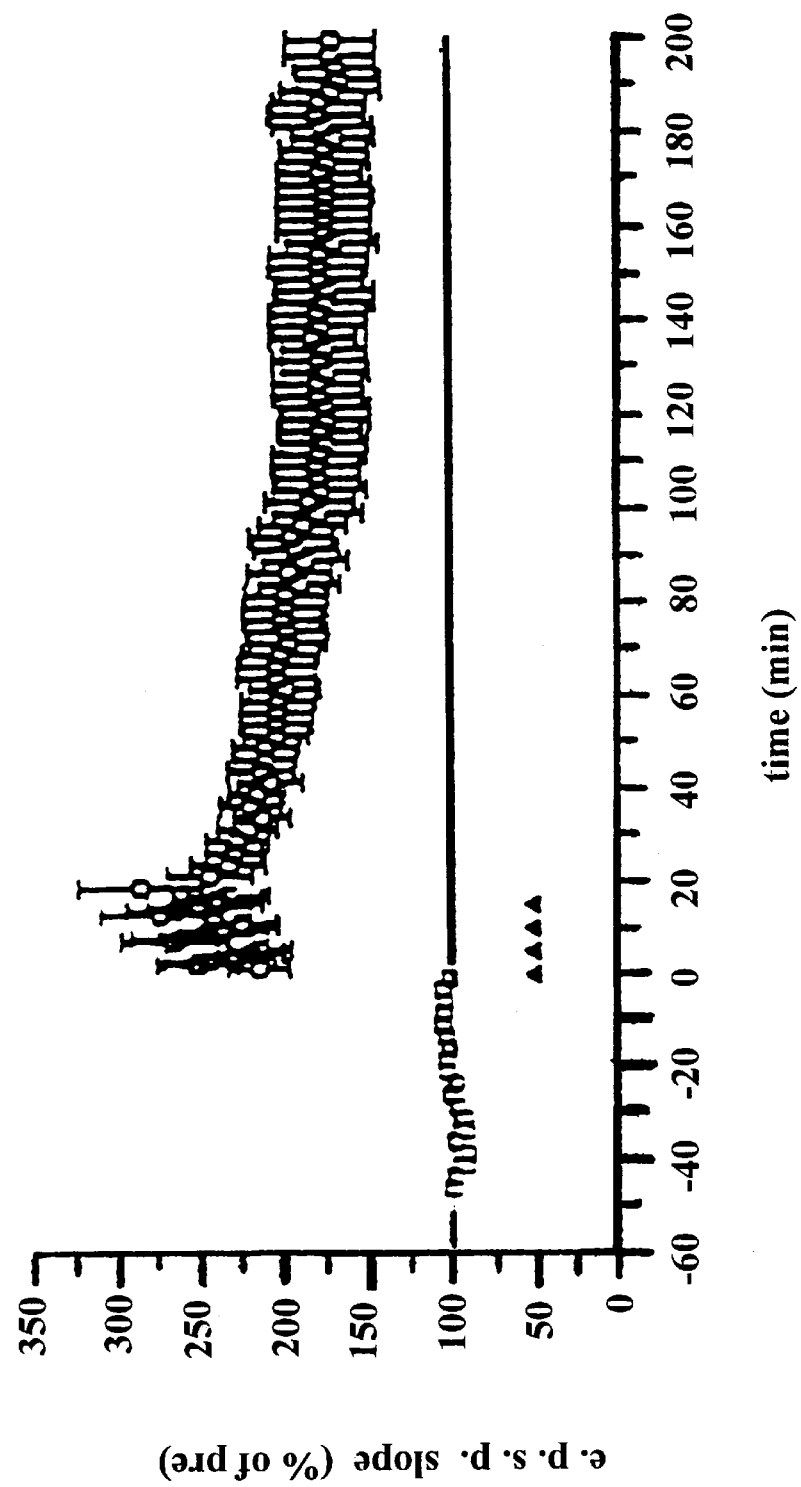
FIGS. 3A–D: Effects of neurotrophic factors and a D1/D5 agonist on LTP in young and aged mice.
Figure 3B:
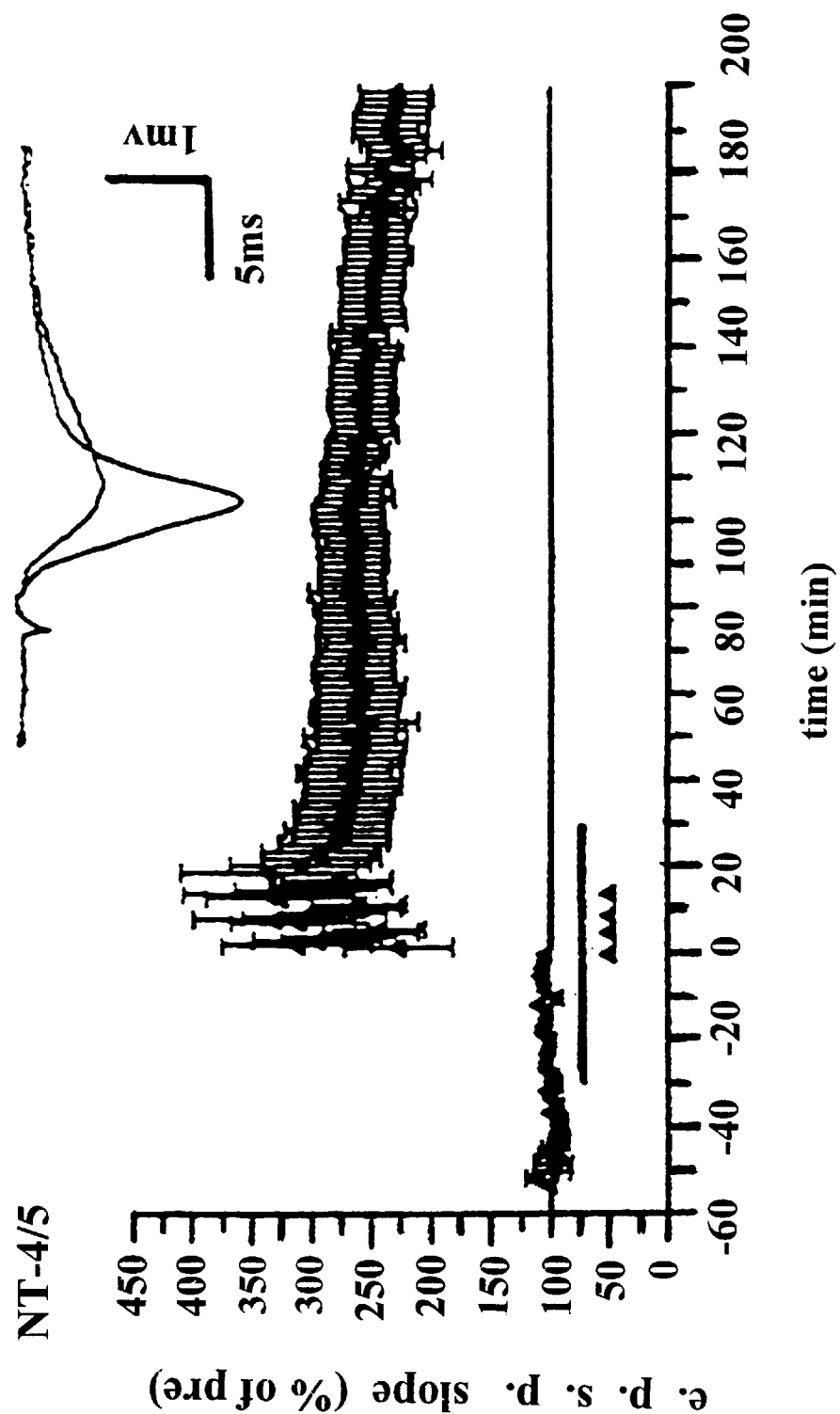
Figure 3C:
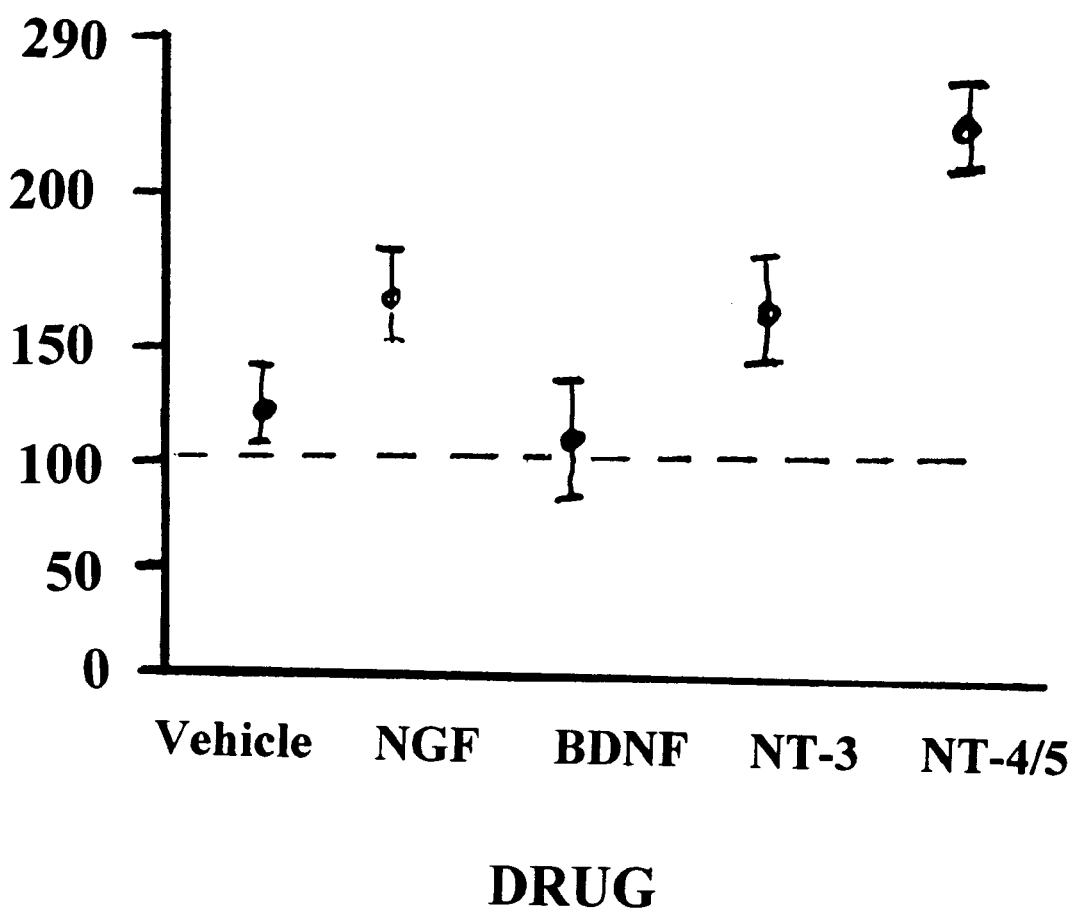
Figure 3D:
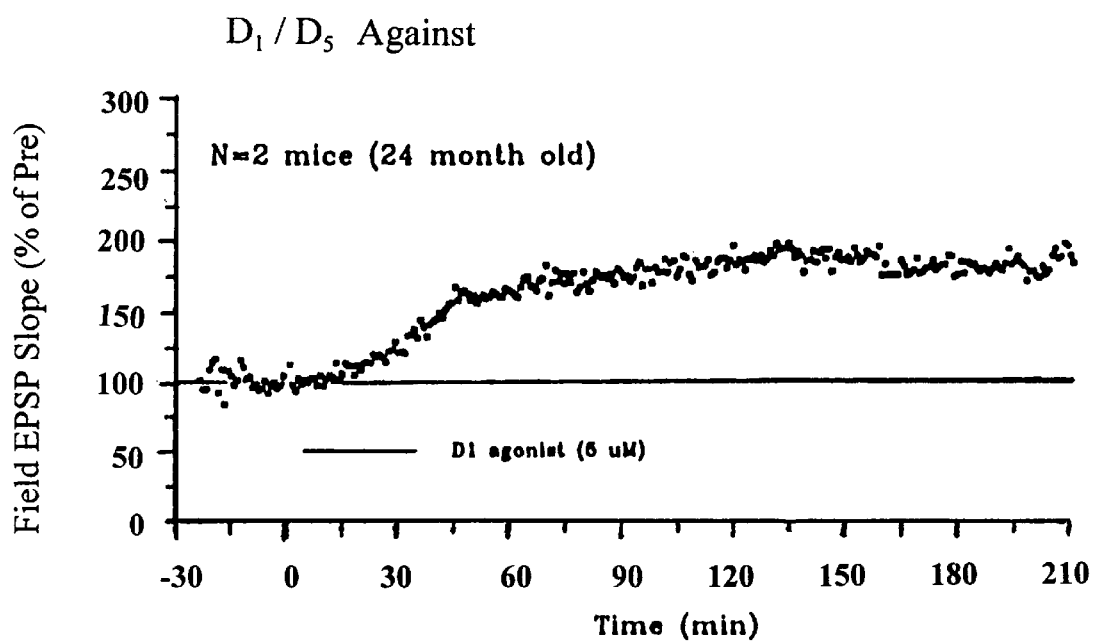

LTP in the CA1 region of the hippocampus contains at least two different phases. The early-phase of LTP (E-LTP) induced by one train tetanus requires activation of the NMDA receptor and several serine-threonine and tyrosine kinases, and lasts 1–3 hours (Bliss & Collingridge, 1993). By contrast, the late-phase of LTP (L-LTP) induced by multiple trains (3–4 trains) requires transcriptional and translational processes, and lasts 6–10 hours (Matthies, 1989; Frey et al., 1992; Huang & Kandel, 1994; Nguyen et al., 1994). Both E-LTP and L-LTP are examined in five different age groups: young, 3 weeks; young adult, 3 months; adult, 6 months; middle-aged, 12 months; and aged, 18–30 months. One train (100 Hz, 1 sec) tetanic stimulation produced similar potentiation in mice of the four different ages (FIGS. 2A–B). There are no significant difference among young, young adult, adult and aged mice (F[3,35]= 0.445, NS), suggesting that the induction mechanism (e.g., NMDA receptor) is not dramatically affected during aging processes. By contrast, L-LTP was completely abolished in aged mice (144.3±10.04%, n=23) (FIG. 2C). In both young adult and adult mice, four trains (100 Hz, 1 sec, with 5-min interval) produces a long-lasting enhancement of synaptic potentials that remains enhanced for at least 3 hours after stimulation. The EPSP was significantly potentiated to 210.31±17.42% (n=19) and 188.1±11.86% (n=8) in young adult and adult mice, respectively. Although L-LTP shows an age-dependent decrease (F[3,63]=4.266, p=0.0083), post-tetanic potentiation (PTP) was not significantly different among four different age groups (F[3,23]=0.63, NS) (FIG. 3D), supporting the idea that the induction mechanism is not altered.

Compound Studies: Age-related hippocampal spatial memory loss correlates with decreases in the level of some neurotrophins.

Figure 4A:
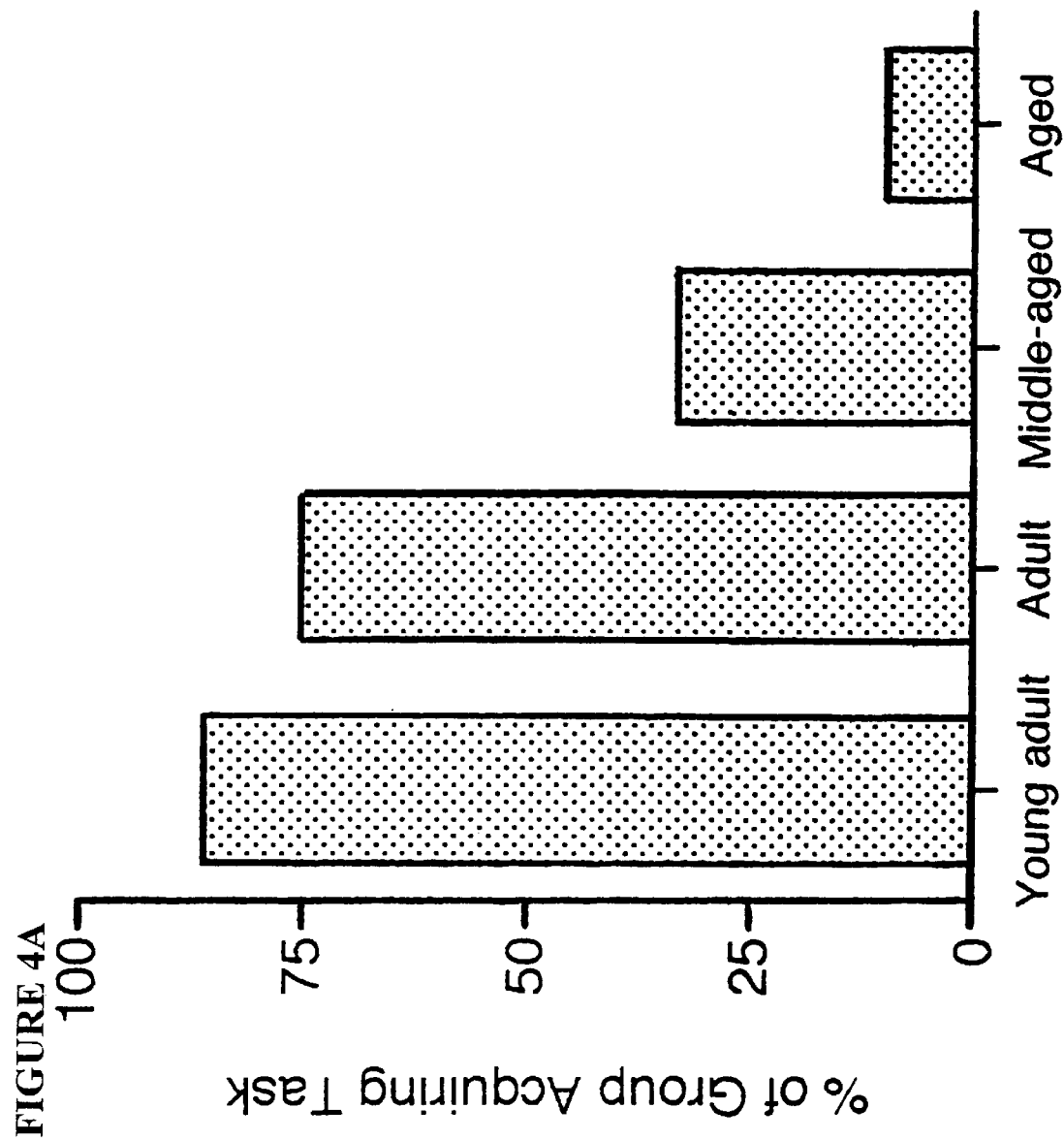
FIGS. 4A–C: Measurement of impaired spatial memory on the Barnes circular maze and its correlation with L-LTP in C57 mice of different age groups.
Figure 4B:
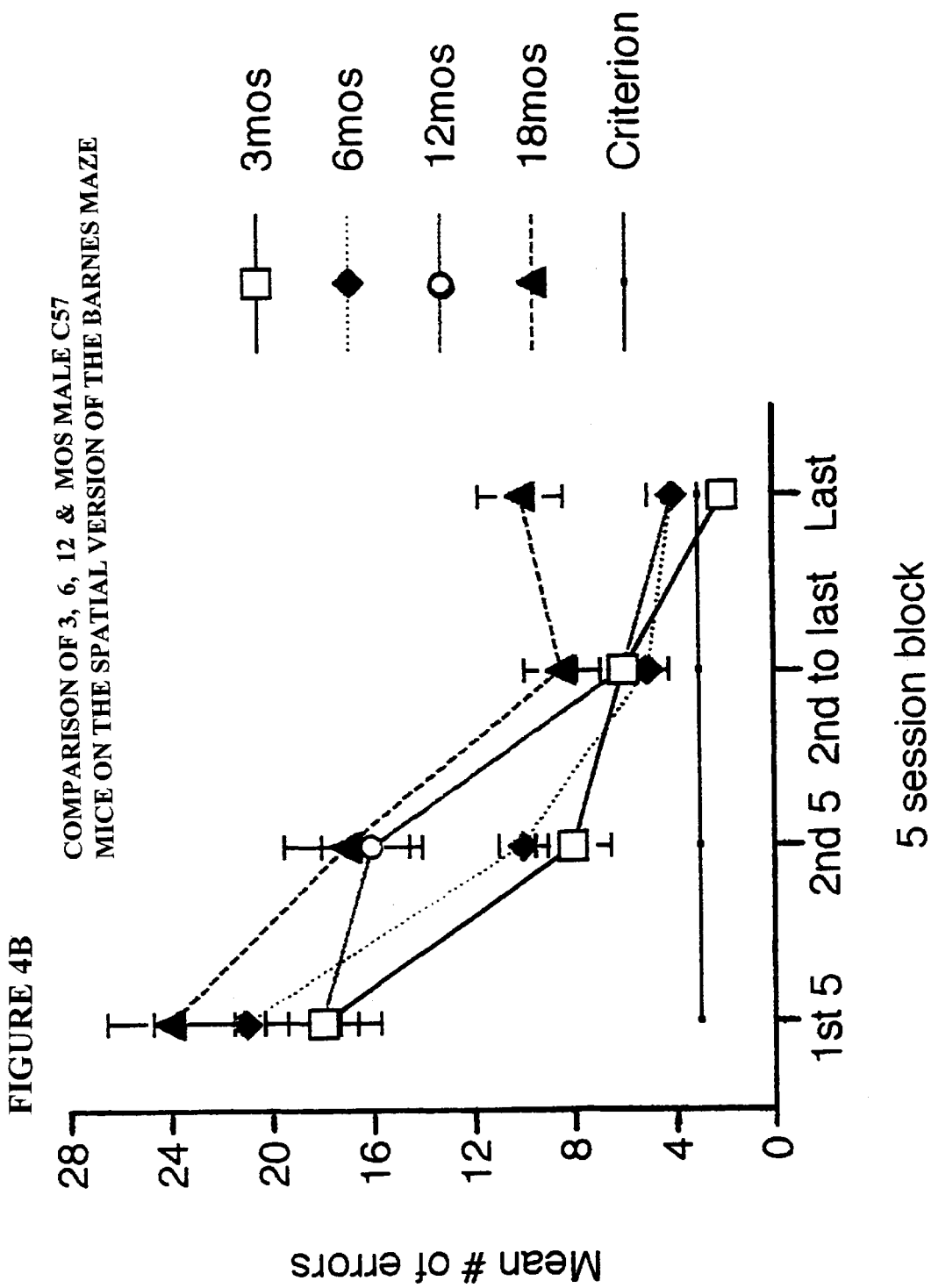
Figure 4C:
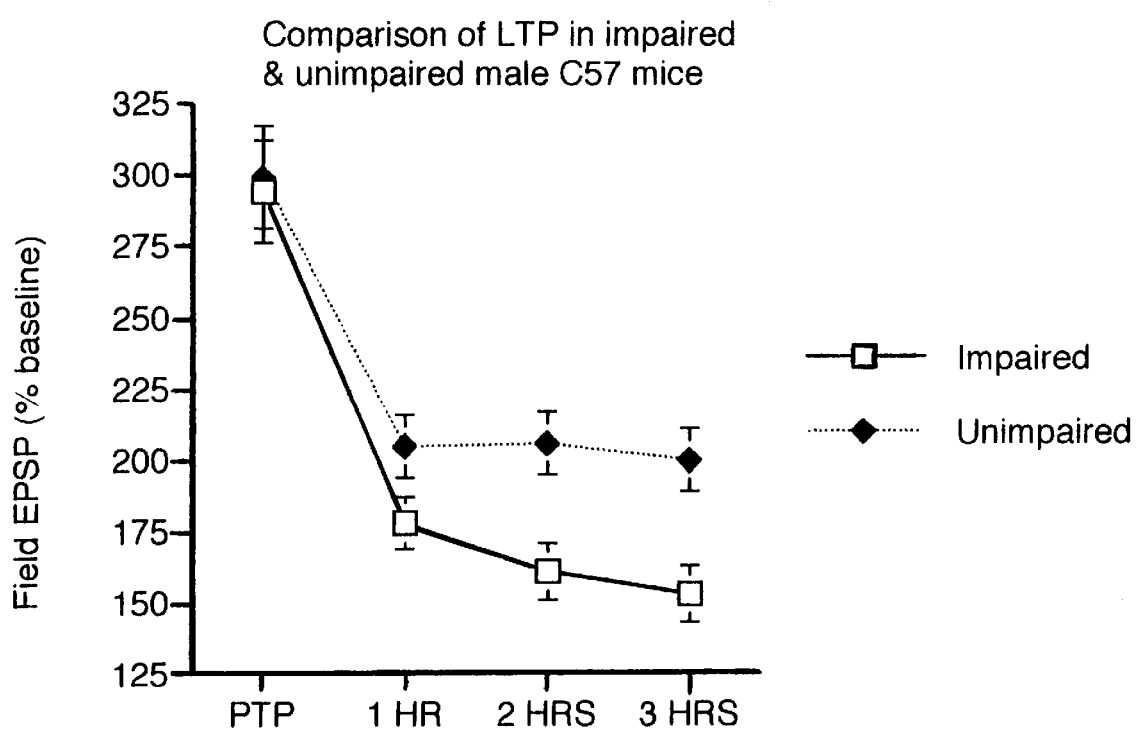

The family of neurotrophic factors contains at least four different known members: nerve growth factor (NGF), brain-derived neurotrophic factor (BDNF), NT-3, and NT-4/5. These neurotrophic factors are distributed widely in the central nervous system, including the hippocampus, and are believed to be involved in various neuronal functions, including synaptic plasticity (Thoenen, 1991; Davies, 1994; Dechent et al., 1994; Klein, 1994). Earlier behavioral studies, upon which studies described herein are based, demonstrated that age-related hippocampal spatial memory loss in old animals is correlated with decreases of the level of some neurotrophins, including NT-4/5 and NGF and NT-3, compensated the loss of memory (Fisher et al., 1991, 1994; Tuszynski and Gage, 1994; Markowska et al., 1994) (FIG. 4C). Since LTP is a likely mechanism involved in animal spatial memeory, whether these neurotrophic factors also compensate for loss of LTP in old mice was the next question examined. In young mice, NT-4/5 (1 ng/ml) produced long-lasting enhancement of synaptic transmission when paired with weak stimulation (25 Hz, 1 sec) (163.0±18.8%, n=6). Neither weak stimulation nor NT-4/5 alone induced significant enhancement (FIG. 4B). This enhancement is frequency dependent, since pairing NT-4/5 with the same amount of pulses but at a lower frequency (0.25 Hz, 100 sec) did not produce potentiation (114.7±30.7%, n=5). Furthermore, NT-4/5 (1 ng/ml) enhanced the potentiation induced by one train of tetanus (230.7±32.8%, n=5). By contrast, one train of tetanus alone produced smaller potentiation (147.0±14.6%, n=7). In old mice, treatment with NT-4/5 (1 ng/ml) reversed the loss of L-LTP in old mice (229.9±30.8%, n=6) (FIG. 4B). The potentiation is significantly greater than that of old mice (t=3.48, p<0.01). By contrast, NT-4/5 did not affect the decrease of paired-pulse facilitation in old mice (FIG. 4B). PTP induced by the first train of tetanus was not different from that induced by NT-4/5 treated or untreated groups.

Previous reports showed that NGF improves behavioral memory in old animals without affecting young animals (Fisher et al., 1991; Markowska et al., 1994). In young mice, NGF (1 ng/ml) paired with weak stimulation did not produce significant potentiation (114.4±15.2%, n=7). In old mice, however, NGF completely reversed the loss of L-LTP (164.0±23.0%, n=7) (FIG. 4A). NGF did not compensate the loss of paired-pulse facilitation. PTP was not affected by NGF treatment. The effects on L-LTP of two neurotrophic factors, BDNF and NT-3 were also tested. NT-3 (1 ng/ml)

compensated for the loss of L-LTP in old mice (NT-3, 157.1± 19.9%, n=5) but BDNF did not (106.7±27.8%, n=5). In either case, basic synaptic transmission, paired-pulse facilitation and post-tetanus potentiation were not effected by NT-3 and BDNF.

The dopamine system in the brain declines during aging. In particular, the level of dopamine decreases in old animals or humans while some of the dopamine receptors remain unchanged (Morgan et al., 1986). Enhancement of the dopamine system improves behavioral memory in old mice (Lorens et al., 1991; Flood et al., 1993). Dopamine or the D1/D5 agonist induces long-lasting enhancement of the CA1 region of the hippocampus in young or adult animals (Gribkoff and Ashe, 1984; Frey et al., 1993; Huang and Kandel, 1994). Therefore, dopamine D1/D5 agonist 6-Br-ApB (5 $\mu$M) induced similar long-lasting enhancement of synaptic responses in both young (n=4) and old (n=3) mice (FIG. 4D). These results suggest that the D1/D5 receptor as well as the subsequent intracellular signal pathway is not significantly affected in old animals.

Behavioral Studies: Impaired spatial memory on the Barnes circular maze in aging C57 mice.

Next animal performance was correlated on the Barnes circular maze with in vitro electrophysiological measurements in the same mice. The spatial memory of aged (18 months) middle-aged (12 months), adult (6 months) and young adult (12 weeks) male C57 mice was assessed using the Barnes circular maze. The maze has 40 holes around the perimeter, one of which leads to a tunnel where the mouse can escape from bright light and a buzzer. Mice were tested once a day to a criterion of 7 out of 8 days with 3 or fewer errors. Most of the young adult and adult mice acquired the task within 40 days whereas most of the aged and middle-aged groups did not. The results suggest that an age-related spatial memory deficit occurs as early as 12 months, that is middle-aged. So, young adult and adult mice were not found to be different from each another. The young adult and adult mice developed a spatial strategy for finding the escape tunnel, whereas the middle-aged and aged mice continued to use a serial search strategy. In addition, the middle-aged and aged mice displayed an initial performance deficit, making more errors and perseverations. To test whether severe sensory, motivational, motor or attention deficits produced the impairment on the spatial version of the Barnes maze, a second group of aged (18 months) and young adult (3 months) mice were tested on a cued version of the task. A deficit in the cued version in the aged mice was not found.

An age-related decline in performance on spatial memory tasks has been correlated with changes in neurotransmitter levels and neuronal degeneration in the hippocampus in rodents. Further, in the hippocampus, age-related changes in synaptic plasticity have also been observed (Ahou et al., 1995). To elucidate which changes in synaptic plasticity contribute to the memory deficits observed during aging, performance on the Barnes circular maze have been correlated with in vitro electrophysiological measurements in the same mice.

Figure 5B:
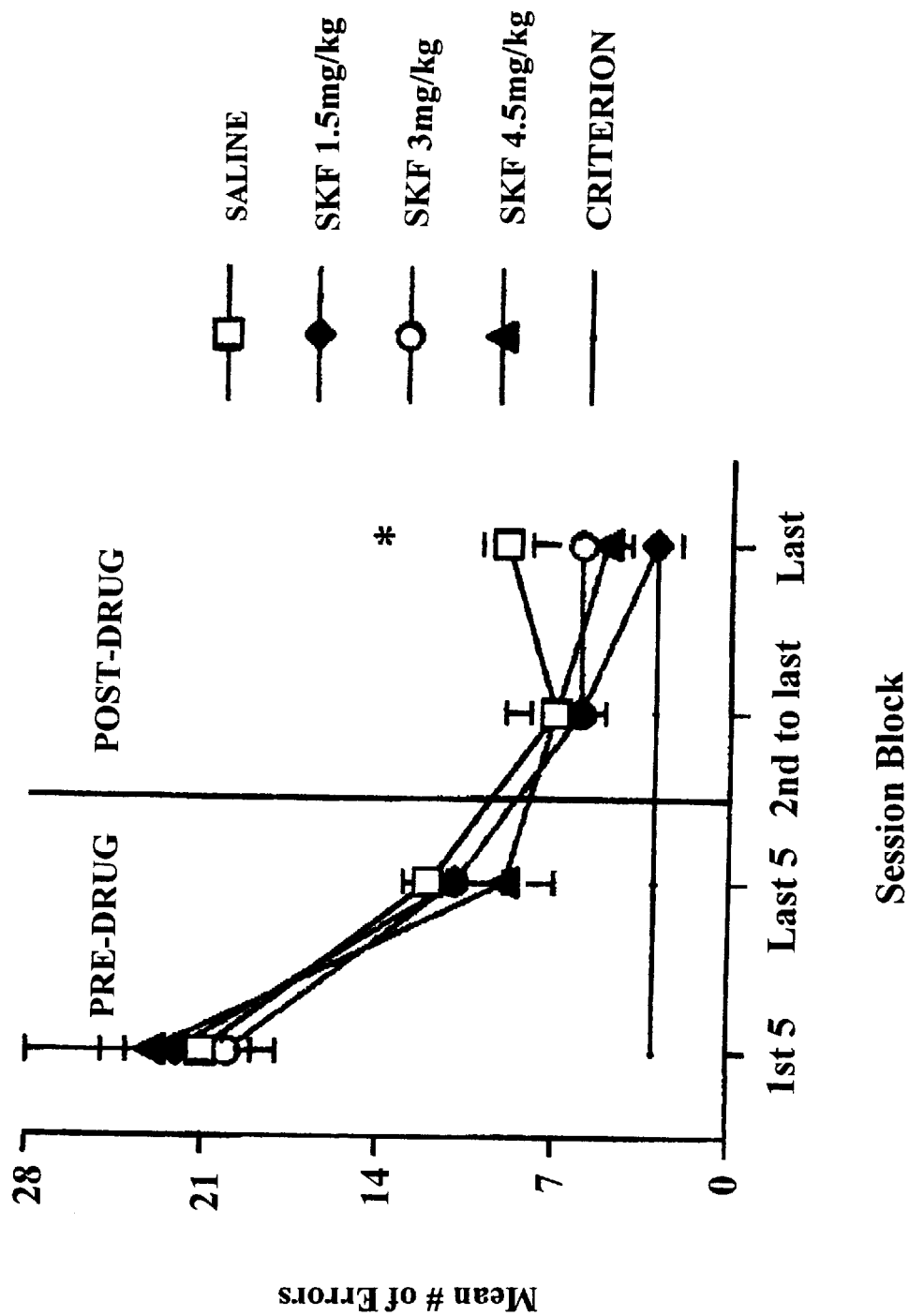

To determine whether D1/D5 agonists could faciliatate spatial learning and memory on the Barnes maze in aged mice, SKF 38393 was administered. During the first 14 sessions no drug was administered and the mean number of errors from sessions 10–14 was calculated. Based on the error scores the aged mice were assigned to the four dose groups (0.0, 1.5, 3.0, 4.5 mg/kg) such that the group error mean for each group was equivalent, e.g. the groups were comprised of mice of equal impairments. Starting on session 15 the mice received daily I.P. injections of SKF 38393 40 minutes prior to testing until they met the learning criterion (7 out of 8 sessions with 3 or fewer errors) or until they reached session 40. See FIGS. 5A and 5B.

Discussion

Previous electrophysiological studies of aging mainly examined the early phase of LTP in rats or mice. Based on these studies, Landfield (1988) and Deupree et al. (1993) reported that LTP is normal in old rats or mice. In contrast, both clinical and experimental behavioral studies consistently show that spatial memory is clearly affected in a majority, if not at all, of the older objects. One possible explanation for this is that other changes in potentiation have not been detected. In fact, LTP can be divided into at least two different phases: an early-phase that is independent of protein synthesis and lasts from 1 to 3 hours; and a late-phase that requires translational and transcriptional processes and lasts from 6 to 10 hours (Frey et al., 1993; Huang and Kandel, 1994; Nguyen et al., 1994). In the present study, L-LTP induced by four trains of tetanus is affected in old mice. By contrast, E-LTP induced by a single train stimulation is the same for variously aged mice.

EXAMPLE 1

Age-Dependent Decreases of Synaptic Transmission and Paired-Pulse Facilitation in the CA1 Region of Hippocampus METHODS: Three-week to 30-month-old C57BJ/6J NIA mice (Charles River Laboratories/National Institute of Aging) or BALB/CJ mice (Jackson Laboratories) were housed and sacrificed in accordance with the guidelines of the Health Sciences Division of Columbia University. Transverse slices of hippocampus (400 mm) were rapidly prepared and maintained at 28° C. in an interface chamber, where they were suffused with artificial cerebrospinal fluid (ACSF) consisting of (in mM): 124 NaCl, 4.0 KCl, 2.0 $CaCl_2$, 1.0 $MgSO_4$, 1.0 $Na_2HPO_3$, 10 glucose, bubbled with 95% $O_2$, 5% $CO_2$. Slices were allowed to recover for at least 2 hrs before experiments were performed. A bipolar tungsten stimulating electrode was placed in the stratum radiatum of the CA1 region or in the stratum pyramidal of the CA3 region. In some experiments, a second independent stimulating electrode was placed in the stratum radiatum of the CA1 region on the other side of the recording microelectrode. Before the start of the experiments, paired-pulse facilitation was tested to verify the independence of the two pathways. Extracellular field potentials were recorded with a glass microelectrode (3–12 megohm, filled with ACSF) placed in the striatum radiatum. The stimulation intensity was alternatively tested at 0.02 Hz. For measuring maximal field EPSPS, the intensity of stimulation was increased until the EPSP magnitude reached a maximal value. For measuring paired-pulse facilitation, the initial magnitude of the first EPSP was adjusted at 1 mV by changing the intensity of stimulation.

EXAMPLE 2

Loss of the Late Phase but not the Early Phase of LTP in Aged Mice

METHODS: The testing synaptic responses were elicited at 0.02 Hz. The stimulation was delivered if the EPSP was stable for at least 30 min (±25%). Two different paradigms were used to induce E-LTP and L-LTP, respectively. One train stimulation, consisting of one 100 Hz for 1 sec at testing intensity, was used to induce E-LTP. Four trains stimulation, consisting of four 100 Hz train for 1 sec at testing intensity with 5-min interval, was used to induce L-LTP. The data were collected for at least 1 hour after stimulation in E-LTP experiments and 3 hours in L-LTP experiments.

EXAMPLE 3

Effects of Neurotrophic Factors and a D1/D5 Agonist on LTP in Young and Aged Mice METHODS: Most drugs were made and stored as concentrated stock solutions and diluted into ACSF on the day of the experiment. NGF and NT-4/5, BDNF and NT-3 were utilized. 8-Br-ApB was purchased from RBI and dissolved in DMSO. The final concentration of DMSO in diluted saline is less than 0.1%.

REFERENCES

Abuchowski et al., In: "Enzymes as Drugs", Holcenberg et al., eds. Wiley-Interscience, New York, N.Y., 367–383 (1981).
Barnes, C. A. *Neurobiol. Aging* 9, 563–568 (1988).
Barnes, C. A. *Trends Neurosci.* 17, 13–18 (1994).
Bliss, T. V. P. & Collingridge, G. L. *Nature* 361, 31–39 (1993).
Carpenter et al., *Toxicol. Appl. Pharmacol.*, 18:35–40 (1971).
Davies, A. M. *Nature* 368, 193–194 (1994).
Dechant, G., Rodriguez-Tébar, A. & Barde, Y.-A. *Prog. Neurobiol.* 42, 347–352 (1994).
Deupree, D. L., Turner, D. A. & Watters, C. L. *Brain Res.* 554, 1–9 (1991).
Dudek, S. M. & Bear, M. F. *Proc. Natl. Acad. Sci. USA* 89, 4363–4367 (1992).
Fischer, W., Bjorklund, A., Chen, K. & Gage, F. H. *J. Neurosci.* 11, 1889–1906 (1991).
Fischer, W., Chen, K. S., Gage, F. H. & Bjorklund, A. Neurobiol. *Aging* 13, 9–23 (1992).
Fischer, W., Sirevaag, A., Wiegand, S. J., Lindsay, R. M. & Bjorklund, A. *Proc. Natl. Acad. Sci. USA* 91, 8607–8611 (1994).
Fischer, W., Wictorin, K., Bjorklund, A., Williams, L. R., Baron, S. & Gage F. H. *Nature* 329, 65–68 (1987).
Frey, U., Huang, Y.-Y. & Kandel, E. R. *Science* 260, 1661–1664 (1993).
Gage, F. H., Dunnet, S. B. & Bjorklund, A. *Neurobiol. Aging* 10, 347–352 (1989).
Huang, Y.-Y. & Kandel, E. R. *Learning & Memory* 1, 74–82 (1994).
Katre et al., *Proc. Natl. Acad. Sci. USA* 84:1487–1491 (1987).
Klein, R. *FASEB J.* 8, 738–7440 (1994).
Larsen, E. et al. *NeuroReport* 4, 895–898 (1993).
Moore, C. I.,Browning, M. D. & Rose, G. M. *Hippocampus* 3, 57–66 (1993).
Morgan, D. G., May, P. C. & Finch, C. E. *JAGS* 35, 334–345 (1986).
Newmark et al., *J. Appl. Biochem.* 4:185–189 (1982).
Nguyen, P. V., Abel, T. & Kandel, E. R. *Science* 265, 1104–1107 (1994).
O'Dell, T. J. & Kandel, E. R. *Learning & Memory* 1, 129–139 (1994).
Squire, L. R. *Psychol. Rev.*, 99, 152–231 (1992).
Squire, L. R. & Zola-Morgan, S. *Science* 253, 1380–1386 (1991).
Timmusk, T., Belluardo, N., Metsis, M. & Persson, H. *Eur. J. Neurosci.* 5, 605–613 (1993).
Tuszynski, M. F. & Gage, F. H. *Ann. Neurol. Suppl.* 35, S9–S12 (1994).
Zafra, F., Castren, E., Thoenen, H. & Lindholm, P. *Proc. Natl. Acad. Sci. USA* 88, 10037–10041 (1991).

What is claimed is:

1. A method to determine the extent of neuronal degradation due to aging, a learning disability, or a neurological disorder, which comprises:
    (a) stimulating a neuronal cell population from a sacrificed non-human animal suffering from neuronal degradation with a stimulation of four pulse trains each of which is about 100 Hertz, for about 1 second, with about 0.2 millisecond individual pulse duration, so as to induce a late-phase long term potentiation that is sustained longer than 3 hours following the stimulation;
    (b) stimulating a neuronal cell population from a sacrificed normal non-human animal with a stimulation of four pulse trains each of which is about 100 Hertz, for about 1 second, with about 0.2 millisecond individual pulse duration, so as to induce a late-phase long term potentiation that is sustained longer than 3 hours following the stimulation; and
    (c) comparing the duration of the late-phase long term potentiation of the neuronal cell population in step (a) with that of the neuronal cell population of step (b) so as to determine if there is a decrease in the duration of late-phase long term potentiation of the neuronal cell population in step (a) and thus determine the extent of neuronal degradation due to aging, the learning disability, or the neurological disorder.

2. The method of claim 1, wherein the neuronal cell population of step (a) is an aged neuronal cell population.

3. The method of claim 1, wherein the neuronal cell population of step (a) is a neuronal cell population associated with a neurological disorder.

4. The method of claim 1, wherein the neuronal cell population of step (a) is a neuronal cell population associated with a learning disability.

5. The method of claim 1, wherein the neuronal cell population of step (a) is obtained from a subject having experienced electroshock or other neurological trauma.

6. The method of claim 1, wherein the neuronal cell population of step (a) is from the CA1 or CA3 region of the hippocampus.

7. The method of claim 1, wherein the four pulse trains are performed at about 5 minute intervals.

8. The method of claim 1, wherein the learning disability or neurological disorder is electric shock induced amnesia or amnesia.

9. A method for determining if a compound increases the duration of late-phase long term potentiation which comprises:
    (a) contacting a neuronal cell population of a sacrificed non-human animal with the compound under suitable conditions;
    (b) stimulating the neuronal cell population of step (a) with a stimulation of four pulse trains each of which is about 100 Hertz, for about 1 second, with about 0.2 millisecond individual pulse duration, so as to induce a late-phase long term potentiation that is sustained longer than 3 hours following the stimulation; and
    (c) comparing the duration of the late-phase long term potentiation of the neuronal cell population of step (b) with that of the duration in the absence of compound so as to determine if the compound increases the duration of late-phase long term potentiation.

10. A method for diagnosing a cognitive disorder of memory or a learning disability which comprises:
(a) stimulating a neuronal cell population of a sacrificed non-human animal and a control neuronal cell population from a normal sacrificed non-human animal with a stimulation of four pulse trains each of which is about 100 Hertz, for about 1 second, with about 0.2 millisecond individual pulse duration, so as to induce a late-phase long term potentiation that is sustained longer than 3 hours following the stimulation;
(b) measuring the duration of the late-phase long term potentiation of each neuronal cell population of step (a) and comparing one to the other, thus diagnosing the cognitive disorder of memory or the learning disability in the subject, wherein a reduction in the duration of late-phase long term potentiation is associated with a cognitive disorder of memory or a learning disability.

11. The method of claim 10, wherein the cognitive disorder is electric shock induced amnesia or amnesia.

* * * * *